United States Patent [19]

Scates et al.

[11] Patent Number: 4,894,477

[45] Date of Patent: Jan. 16, 1990

[54] PROCESS FOR REGENERATING A CARBONYLATION CATALYST SOLUTION TO REMOVE CORROSION METALS AND CARBONYLATION OF METHANOL TO ACETIC ACID

[75] Inventors: Mark O. Scates, Pearland; G. P. Torrence, Corpus Christi; Ronny G. Wood, Houston, all of Tex.

[73] Assignee: Hoechst Celanese Corporation, Sommerville, N.J.

[21] Appl. No.: 918,740

[22] Filed: Oct. 14, 1986

[51] Int. Cl.$^4$ .................... C07C 51/12; C07C 53/08; C07C 51/47

[52] U.S. Cl. .................................... 562/519; 502/12; 562/608

[58] Field of Search .................... 562/519, 608; 502/12

[56] References Cited

U.S. PATENT DOCUMENTS 4,007,130 2/1977 Leach et al. ........................ 502/12
4,410,449 10/1983 Diessel et al. ............... 562/608 X R

*Primary Examiner*—Vivian Garner
*Attorney, Agent, or Firm*—Donald R. Cassady, Depaoli & O'Brien

[57] ABSTRACT

A process for treating carbonylation catalyst solutions which contain a rhodium component and a lithium component to remove metallic corrosion products comprises contacting the catalyst solution with a cation exchange resin in the lithium form.

18 Claims, 1 Drawing Sheet

PROCESS FOR REGENERATING A CARBONYLATION CATALYST SOLUTION TO REMOVE CORROSION METALS AND CARBONYLATION OF METHANOL TO ACETIC ACID

BACKGROUND OF THE INVENTION

1. Field of the Invention

This invention relates generally to an improvement in the process for carbonylating methanol to acetic acid in the presence of a rhodium-containing catalyst. More particularly, the invention relates to an improved process for regenerating the catalyst solution employed in the carbonylation reaction.

2. Description of the Prior Art

Among currently-employed processes for synthesizing acetic acid one of the most useful commercially is the catalyzed carbonylation of methanol with carbon monoxide as taught in U.S. Pat. No. 3,769,329 issued to Paulik et al on Oct. 30, 1973. The carbonylation catalyst comprises rhodium, either dissolved or otherwise dispersed in a liquid reaction medium or else supported on an inert solid, along with a halogen-containing catalyst promoter as exemplified by methyl iodide. The rhodium can be introduced into the reaction system in any of many forms, and it is not relevant, if indeed it is possible, to identify the exact nature of the rhodium moiety within the active catalyst complex. Likewise, the nature of the halide promoter is not critical. The patentees disclose a very large number of suitable promoters, most of which are organic iodides. Most typically and usefully, the reaction is conducted with the catalyst being dissolved in a liquid reaction medium through which carbon monoxide gas is continuously bubbled.

An improvement in the prior-art process for the carbonylation of an alcohol to produce the carboxylic acid having one carbon atom more than the alcohol in the presence of a rhodium catalyst is disclosed in copending, commonly assigned U.S. patent application Ser. No. 699,525, filed Feb. 8, 1985 and European patent application 161,874; published Nov. 21, 1985. As disclosed therein acetic acid (HOAc) is produced from methanol (MeOH) in a reaction medium comprising methyl acetate (MeOAc), methyl halide, especially methyl iodide, (MeI), and rhodium present in a catalytically-effective concentration. The invention therein resides primarily in the discovery that catalyst stability and the productivity of the carbonylation reactor can be maintained at surprisingly high levels, even at very low water concentrations, i.e. 4 wt. % or less, in the reaction medium (despite the general industrial practice of maintaining approximately 14 wt. % or 15 wt. % water) by maintaining in the reaction medium, along with a catalytically-effective amount of rhodium, at least a finite concentration of water, methyl acetate and methyl iodide, a specified concentration of iodide ions over and above the iodide content which is present as methyl iodide or other organic iodide. The iodide ion is present as a simple salt, with lithium iodide being preferred. The applications teach that the concentration of methyl acetate and iodide salts are significant parameters in affecting the rate of carbonylation of methanol to produce acetic acid especially at low reactor water concentrations. By using relatively high concentrations of the methyl acetate and iodide salt, one obtains a surprising degree of catalyst stability and reactor productivity even when the liquid reaction medium contains water in concentrations as low as about 0.1 wt. %, so low that it can broadly be defined simply as "a finite concentration" of water. Furthermore, the reaction medium employed improves the stability of the rhodium catalyst, i.e. resistance to catalyst precipitation, especially during the product-recovery steps of the process wherein distillation for the purpose of recovering the acetic acid product tends to remove from the catalyst the carbon monoxide which in the environment maintained in the reaction vessel, is a ligand with stabilizing effect on the rhodium. U.S. patent application Ser. No. 699,525 is herein incorporated by reference.

In operation of the process for the carbonylation of methanol to acetic acid on a continuous basis, a solution containing the soluble catalyst complex is separated from the reactor effluent and recycled to the reactor. However, with operation over extended periods of time, corrosion products, namely, iron, nickel, molybdenum, chromium and the like form and build up in the catalyst recycle stream. Such foreign metals, if present in sufficient quantity, are known to interfere with the carbonylation reaction or accelerate competing reactions such as the water-gas reaction (carbon dioxide and hydrogen formation) and methane formation. Thus, the presence of these corrosion metal contaminants has an adverse effect on the process, in particular, a consequent loss in yield based on carbon monoxide. Further, foreign metals can react with ionic iodine thus making this component of the catalytic system unavailable for reaction with rhodium and causing instability in the catalyst system. In view of the high cost of the rhodium-containing catalyst, replacement of spent catalyst can be effected only at a prohibitive cost. Consequently, a method for regeneration of the catalyst is not only desirable but necessary.

According to U.S. Pat. No. 4,007,130, a carbonylation catalyst solution comprising the complex reaction product of a rhodium component or an iridium component, a halogen component and carbon monoxide which contains metallic corrosion products is intimately contacted with a cation exchange resin in its hydrogen form and the catalyst solution recovered free of the metallic corrosion products. As disclosed therein, the contacting is effected by passing the catalyst solution containing the undesirable corrosion metal contaminants through a bed of the cation exchange resin and recovering as the effluent from the bed the catalyst solution containing the complex rhodium or iridium component but substantially free of the corrosion products which are adsorbed on and removed by the resin bed. Upon exhaustion as indicated by breakthrough of the corrosion metal products in the effluent, the resin bed is regenerated by treatment with a mineral acid such as hydrochloric, sulfuric, phosphoric or hydriodic acid and reused.

However, U.S. Pat. No. 4,007,130 does not contemplate using the catalyst solutions such as set forth in the aforementioned U.S. patent application Ser. No. 699,525. Thus, in the improved catalyst solutions as previously discussed, there is present a specified concentration of iodide ions over and above the iodide content which is present as methyl iodide or other organic iodide. This additional iodide ion is present as a simple salt, and most preferably, as lithium iodide. What has been discovered is that in regenerating the catalyst solution in order to remove the metal contaminants by means of passing the catalyst solution through a bed of a cation exchange resin in the hydrogen form as disclosed in U.S. Pat. No. 4,007,130, the lithium ion in the catalyst solution is also reduced. The removal of the lithium ion from the catalyst solution greatly reduces the reactivity and stability of the reaction medium.

Accordingly, it is necessary to provide an improved process for regenerating carbonylation catalyst solutions which contain lithium to allow the removal of corrosion metal contaminants from the catalyst solutions and to avoid the removal of the desirable components from such solutions. It is therefore an object of the present invention to provide a process for treating carbonylation catalyst solutions containing lithium to remove metallic corrosion products therefrom and to recover the catalyst solution in a form suitable for return to the process as an active catalyst without the need for excessive replacement of the components therein.

SUMMARY OF THE INVENTION

According to the process of the present invention, a catalyst solution comprising rhodium and a finite concentration of lithium ions and which is contaminated with corrosion metals is intimately contacted with a cation exchange resin in its lithium form and a catalyst solution is recovered free of the metallic contaminants and without drastic reductions in the lithium content. Generally, the contacting is effected by passing the catalyst solution containing the undesirable metal contaminants through a bed of the cation exchange resin in the $Li^{30}$ form and recovering as the effluent from the bed the catalyst solution containing the rhodium component and lithium but substantially freed of the corrosion products which are removed by the resin bed. Upon exhaustion of the ion exchange resin, the resin bed can be regenerated by treatment with a lithium salt such as lithium acetate and reused.

BRIEF DESCRIPTION OF THE DRAWING

The Figure is a schematic diagram illustrating the flow of process streams used in the catalytic carbonylation of methanol to acetic acid and the removal of metallic corrosion products from the process streams.

DETAILED DESCRIPTION OF THE INVENTION

Figure 1:
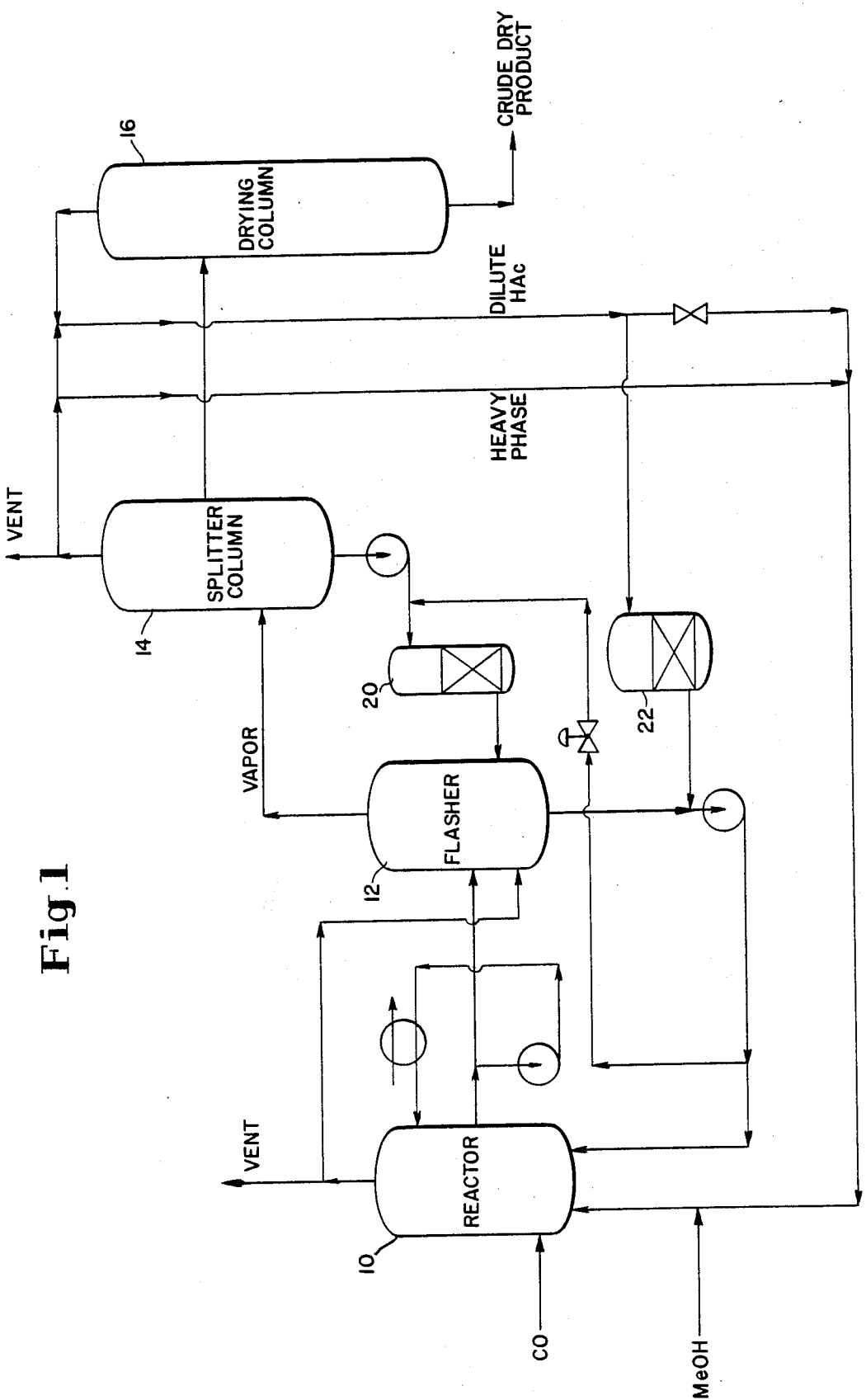

The process of the present invention is applicable to the regeneration of catalyst solutions containing soluble rhodium complexes and metallic contaminants such as iron, nickel, chromium and molybdenum. The catalyst solutions to which the regeneration technique of the invention is particularly applicable are those which are useful for the carbonylation of methanol to acetic acid under low water conditions such as set out in U.S. patent application Ser. No. 699,525. Thus, the catalyst solutions to be regenerated in accordance with the process of the present invention will contain the rhodium catalyst and lithium which is present as a lithium iodide salt.

In the low water carbonylation of methanol to acetic acid as exemplified in U.S. patent application Ser. No. 699,525, the catalyst which is employed includes a rhodium component and a halogen promoter in which the halogen is either bromine or iodine. Generally, the rhodium component of the catalyst system is believed to be present in the form of a coordination compound of rhodium with a halogen component providing at least one of the ligands of such coordination compound. In addition to the coordination of rhodium and halogen, it is also believed that carbon monoxide ligands form coordination compounds or complexes with rhodium. The rhodium component of the catalyst system may be provided by introducing into the reaction zone rhodium in the form of rhodium metal, rhodium salts and oxides, organic rhodium compounds, coordination compounds of rhodium, and the like.

The halogen promoting component of the catalyst system consists of a halogen compound comprising an organic halide. Thus, alkyl, aryl, and substituted alkyl or aryl halides can be used. Preferably, the halide promoter is present in the form of an alkyl halide in which the alkyl radical corresponds to the alkyl radical of the feed alcohol which is carbonylated. For example, in the carbonylation of methanol to acetic acid, the halide promoter will comprise methyl halide, and more preferably methyl iodide.

The liquid reaction medium employed may include any solvent compatible with the catalyst system and may include pure alcohols, or mixtures of the alcohol feedstock and/or the desired carboxylic acid and/or esters of these two compounds. The preferred solvent and liquid reaction medium for the low water carbonylation process comprises the carboxylic acid product. Thus, in the carbonylation of methanol to acetic acid, the preferred solvent is acetic acid.

Water is also added to the reaction medium, but, at concentrations well below what has heretofore been thought practical for achieving sufficient reaction rates. It is known that in rhodium-catalyzed carbonylation reactions of the type set forth in this invention, the addition of water exerts a beneficial effect upon the reaction rate (U.S. Pat. No. 3,769,329). Thus, commercial operations run at water concentrations of at least 14 wt. %. Accordingly, it is quite unexpected that reaction rates substantially equal to and above reaction rates obtained with such high levels of water concentration can be achieved with water concentrations below 14 wt. % and as low as 0.1 wt. %.

In accordance with the carbonylation process useful in the present invention, the desired reaction rates are obtained even at low water concentrations by including in the reaction medium an ester which corresponds to the alcohol being carbonylated and the acid product of the carbonylation reaction and an additional iodide ion which is over and above the iodide which is present as a catalyst promoter such as methyl iodide or other organic iodide. Thus, in the carbonylation of methanol to acetic acid, the ester is methyl acetate and the additional iodide promoter is an iodide salt, e.g., lithium iodide. It has been found that under low water concentrations, methyl acetate and lithium iodide act as rate promoters only when relatively high concentrations of each of these components are present and that the promotion is higher when both of these components are present simultaneously. This has not been recognized in the prior art previous to disclosure of commonly assigned U.S. patent application Ser. No. 699,525. The concentration of lithium iodide used in the reaction medium of the present invention is believed to be quite high as compared with what little prior art there is dealing with the use of halide salts in reaction systems of this sort.

The low water carbonylation catalyst solutions are useful in carbonylating other alcohols besides methanol. Thus, useful feedstocks which can be carbonylated include alkanols containing 1-20 carbon atoms. Preferred feedstocks are alkanols containing 1-10 carbon atoms, and more preferred are alkanols of 1-5 carbon atoms. Methanol is the particularly preferred feed and is converted to acetic acid.

The carbonylation reaction may be carried out by intimately contacting the above defined feed alcohol, which is in the liquid phase, with gaseous carbon monoxide bubbled through a liquid reaction medium containing the rhodium catalyst, halogen-containing promoting component, alkyl ester, and additional soluble iodide salt promoter, at conditions of temperature and pressure suitable to form the carbonylation product. Thus, if the feed is methanol, the halogen-containing promoting component will comprise methyl iodide and the alkyl ester will comprise methyl acetate. It will be generally recognized that it is the concentration of iodide ion in the catalyst system that is important and not the cation associated with the iodide, and that at a given molar concentration of iodide the nature of the cation is not as significant as the effect of the iodide concentration. Any metal iodide salt, or any iodide salt of any organic cation, can be used provided that the salt is sufficiently soluble in the reaction medium to provide the desired level of the iodide. The iodide salt can be a quaternary salt of an organic cation or the iodide salt of an inorganic cation, preferably it is an iodide salt of a member of the group consisting of the metals of Group Ia and Group IIa of the periodic table as set forth in the "Handbook of Chemistry and Physics" published by CRC Press, Cleveland, Ohio, 1975-76 (56th edition). In particular, alkali metal iodides are useful, with lithium iodide being preferred. It is, however, the use of lithium iodide and the inadvertent loss thereof during removal of metal contaminants from catalyst solutions by ion exchange which is the problem directly solved by the catalyst regeneration process of this invention.

Typical reaction temperatures for carbonylation will be approximately 150°-250° C., with the temperature range of about 180°-220° C. being the preferred range. The carbon monoxide partial pressure in the reactor can vary widely but is typically about 2-30 atmospheres, and preferably, about 4-15 atmospheres. Because of the partial pressure of by-products and the vapor pressure of the contained liquids, the total reactor pressure will range from about 15 to 40 atmospheres.

A reaction system which can be employed, in the present improved catalyst regeneration process is shown in the Figure and comprises a liquid-phase carbonylation reactor 10, a flasher 12, and a methyl iodide-acetic acid splitter column 14. The carbonylation reactor 10 is typically a stirred autoclave within which the reacting liquid contents are maintained automatically at a constant level. Into this reactor there are continuously introduced fresh methanol, sufficient water to maintain at least a finite concentration of water in the reaction medium, recycled catalyst solution from the flasher base, and recycled methyl iodide and methyl acetate from the overhead of methyl iodide-acetic acid splitter column 14. Alternate distillation systems can be employed so long as they provide means for recovering the crude acetic acid and recycling to the reactor catalyst solution, methyl iodide, and methyl acetate. In the preferred process, a mixed carbon monoxide feed is continuously introduced into carbonylation reactor 10 just below the agitator which is used to stir the contents. The gaseous feed is, of course, thoroughly dispersed through the reacting liquid by this means. A gaseous purge stream is vented from the reactor to prevent buildup of gaseous by-products and to maintain a set carbon monoxide partial pressure at a given total reactor pressure. The temperature of the reactor is controlled automatically, and the carbon monoxide feed is introduced at a rate sufficient to maintain the desired total reactor pressure.

Liquid product is drawn off from carbonylation reactor 10 at a rate sufficient to maintain a constant level therein and is introduced to flasher 12 at a point intermediate between the top and bottom thereof. In flasher 12 the catalyst solution is withdrawn as a base stream (predominantly acetic acid containing the rhodium and the iodide salt along with lesser quantities of methyl acetate, methyl iodide, and water), while the overhead of flasher 12 comprises largely the product acetic acid along with methyl iodide, methyl acetate, and water. A portion of the carbon monoxide along with gaseous by-products such as methane, hydrogen, and carbon dioxide exits the top of flasher 12.

The product acetic acid drawn from the base of methyl iodide-acetic acid splitter column 14 (it can also be withdrawn as a side stream near the base as shown in the Figure) is then drawn off for final purification as desired by methods which are obvious to those skilled in the art and which are outside the scope of the present invention. Drying column 16 is one means of purification. The overhead from methyl iodide-acetic acid splitter 14, comprising mainly methyl iodide and methyl acetate, is recycled to carbonylation reactor 10 along with fresh methyl iodide, the fresh methyl iodide being introduced at a rate sufficient to maintain in the carbonylation reactor the desired concentration of methyl iodide in the liquid reaction medium. The fresh methyl iodide is needed to compensate for small losses of methyl iodide in the flasher and carbonylation reactor vent streams. Typically, the overhead from methyl iodide-acetic acid splitter will contain a heavy phase of aqueous methyl iodide and methyl acetate and a light phase comprising aqueous acetic acid. Any water from the purification stage which will contain small amounts of acetic acid can be combined with the light aqueous acetic acid phase from splitter 14 for return to reactor 10.

It has been found that metal contaminants, in particular, iron, nickel, chromium and molybdenum can be present in any of the process streams as just previously described. The accumulation of these metal contaminants has an adverse effect on the rate at which acetic acid is produced and the stability of the process, in general. Accordingly, ion exchange resin beds are placed within the processing scheme to remove these metal contaminants from the processing streams. In the Figure, ion exchange resin bed 20 is placed to remove corrosion metal contaminants from the catalyst solution recycled from the flasher base to the reactor 10. Ion exchange bed 22 is placed to remove corrosion metal contaminants from the combined aqueous acetic acid stream and, thus, prevents corrosion metal ingress to the catalyst solution. It should be understood, that any of the process streams can be treated with the ion exchange resin beds to remove metal contaminants therefrom. The only criteria necessary is that the processing stream be at a temperatures which does not deactivate the resin. Generally, the processing streams which are treated will have a finite concentration of the rhodium catalyst and/or lithium cation from the additional lithium iodide salt which is added as a catalyst promoter.

The resins useful for regenerating the catalyst solutions according to the present invention are cation exchange resins either of the strong-acid or the weak-acid type in their lithium form. Both types are readily available as commercial products. The weak-acid cation exchange resins are mostly copolymers of acrylic or methacrylic acids or esters or the corresponding nitriles but a few of those marketed are phenolic resins. Strong-acid cation exchange resins which are the resins preferred for use in the present invention are constituted predominantly of sulfonated styrene-divinylbenzene copolymers although some of the available resins of this type are phenol-formaldehyde condensation polymers. Either the gel type or the macroreticular type resin is suitable but the latter is preferred since organic components are present in the catalyst solutions being treated.

Contacting of the metal-contaminated catalyst solutions and the resin can be effected in a stirred vessel wherein the resin is slurried with the catalyst solution with good agitation and the catalyst solution is then recovered by decantation, filtration, centrifuging, etc. However, treatment of the catalyst solutions is usually effected by passing the metal-contaminated solution through a fixed-bed column of the resin. The catalyst regeneration can be carried out as a batch, semi-continuous or continuous operation either with manual or automatic control employing methods and techniques well known in the art of ion-exchange.

The ion exchange treatment can be effected at temperatures in the range from about 0° to about 120° C., although lower or higher temperatures limited only by the stability of the resin can be employed. Preferred temperatures are those in the range from about 20° to about 90° C. since chromium removal is more efficient at the higher temperatures. At the higher temperatures, a nitrogen or CO purge is desirable. If temperatures above the boiling point of the catalyst solutions are employed, then operation under pressure will be required to maintain the solution in the liquid phase. However, pressure is not a critical variable. Generally, atmospheric pressure or a pressure slightly above atmospheric is employed but superatmospheric or subatmospheric pressures can be used if desired.

The rate of flow of the catalyst solution through the resin during the corrosion metal removal process will, in general, be that recommended by the resin manufacturer and will usually be from about 1 to about 20 bed volumes per hour. Preferably, the flow rates are kept to from about 1 to about 12 bed volumes per hour. After contacting, washing or rinsing of the resin bed with water or the carbonylation product from the process from which the catalyst being treated is derived such as acetic acid is essential for removing all the rhodium from the resin bed. The rinsing or washing is effected at similar flow rates as in the removal step.

After the resin has become exhausted, i.e., when the metal contaminants are breaking through into the effluent, the resin can be regenerated by passing therethrough a solution of lithium salts. Generally, the lithium salt used in the regenerating cycle has a concentration in the range from about 1% to about 20%. Quantities employed and procedures are those well established in the art and recommended by the resin manufacturers. Aqueous lithium acetate is preferred as a regenerating agent since the acetate anion is employed in the reaction system and is readily available for use. A further advantage is that its use eliminates the rinsing step normally required after the regeneration process when other regenerates are employed.

To maximize corrosion metal regeneration capacity and to maximize resin bed column performance at relatively high concentrations of lithium acetate, the lithium acetate regeneration solution should contain some acetic acid to avoid the formation of any insoluble corrosion metal compounds during the regeneration cycle. Precipitation of these compounds during the regeneration cycle could reduce the regeneration performance of the column and also cause plugging of the resin bed. Typically, acetic acid concentrations of from 0.1 to about 95 wt. % can be used, with acetic acid concentrations of from about 0.1 to 20 wt. % being preferred.

The treatment of the catalyst solution can be operated as a batch or a continuous operation. The preferred type of operation is a continuous one wherein a slipstream from a catalyst solution being recycled to the reactor for producing the acids, is withdrawn, passed through the ion-exchange resin, the corrosion products being adsorbed thereon, and the effluent free of said corrosion products is returned to the catalyst recycle stream and thence to the reactor. The ion-exchange operation can be cyclic. As the resin becomes exhausted in one bed, the slipstream of catalyst solution can be diverted to a fresh bed while the exhausted bed is subjected to regeneration.

The invention is illustrated in the following examples which, however, are not to be construed as limiting it in any manner except as it is limited in the appended claims.

EXAMPLE 1

A run to remove corrosion metals from the acetic acid solution leaving the flasher was carried out using in the lithium form a fresh, strong acid cation exchange resin of the sulfonated styrene-divinylbenzene copolymer type known to the trade as "Amberlyst-15", resin manufactured by the Rohm and Haas Co.

A glass column (2 cm ID $\times$ 50 cm) was charged with 53 cc of the resin in the hydrogen form. The resin was supported on a glass frit at the bottom of the column. The resin had been soaked in water for 24 hours before it was loaded in the column, after which the resin bed was backwashed with approximately 4 bed volumes of water to remove fines and classify the resin bed. The resin was converted to the lithium form by passing 200 ml of a 10 wt. % lithium acetate in 1 wt. % acetic acid/99 wt. % water solution through the bed followed by a column rinse with acetic acid. The catalyst solution was then passed through the resin bed until the column capacity for the corrosion metal contaminants was exhausted. The bed was then washed with acetic acid followed by resin regeneration to the lithium form using 200 ml of a 10 wt. % lithium acetate in 1 wt. % acetic acid/99 wt. % water solution. Analysis of corrosion metals in the effluent from the exhaustion, rinse and regeneration cycles indicated effective removal by the lithium form of the resin of the metal contaminants, in particular iron, from the flasher catalyst solution that contained a high concentration of soluble lithium ions. These results are summarized in Table I. Similar results were also obtained after a number of regeneration and exhaustion cycles using lithium acetate in various aqueous acetic acid solutions as the regenerant solution.

TABLE I

Corrosion Metal Removal from Acetic Acid Solution of the Flasher Using Strong Acid Amberlyst-15 Cation Exchange Resin

| Corrosion Metal[b] | Resin Bed Capacity[a] (gms metal/L resin) | | Column Regeneration[c] (%) |
|---|---|---|---|
| | Removal Cycle | Regeneration Cycle | |
| Iron | 13.1 | 12.7 | 97 |
| Nickel | 5.1 | 4.3 | 87 |
| Chromium | 2.1 | 2.6 | 124 |
| Molybdenum | 2.7 | 2.6 | 96 |

[a]Column operated at ambient temperature (25° C.) and atmospheric pressure. Column resin bed volume (BV) is 53 ml. Column flow rate during removal cycle is 1.8 BV/hr Column flow rate during regeneration cycle is 0.8 BV/hr 10 wt. % LiOAc in 1 wt. % HOAc/99 wt. % $H_2O$ is used as the regenerant solution
[b]Flasher catalyst solution contained 4100 ppm Fe, 2100 ppm Ni, 1300 ppm Cr, 700 ppm Mo and 4100 ppm Li.
[c]% column regeneration = (resin bed capacity from regeneration cycle/resin bed capacity from removal cycle × 100.

What is claimed is:

1. A process for the regeneration of carbonylation catalyst solutions containing rhodium and lithium and further containing corrosion metal contaminants which comprises intimately contacting said catalyst solution with a cation exchange resin in the lithium form and recovering a catalyst solution of reduced metal contaminant content.

2. The process of claim 1 wherein said resin is a strong-acid cation exchange resin.

3. The process of claim 1 wherein said contacting is effected by passing the catalyst solution through a fixed-bed column of said resin.

4. The process of claim 1 wherein said resin is regenerated after exhaustion by washing with a lithium salt.

5. The process of claim 4 wherein said lithium salt is lithium acetate.

6. The process of claim 4 wherein said lithium salt is dissolved in a regeneration solution of water and acetic acid.

7. The process of claim 6 wherein said acetic acid comprises from about 0.1 to 95% by weight of said regeneration solution.

8. The process of claim 7 wherein said acetic acid comprises about 0.1 to 20 wt. % of said regeneration solution.

9. The process of claim 6 wherein said lithium acetate is present in amounts of from about 1 to 20 wt. %.

10. In a process for the carbonylation of methanol to acetic acid in a carbonylation reactor by passing carbon monoxide through a reaction medium contained in said reactor and comprising methanol and a catalyst solution of low water content comprising rhodium, a methyl iodide promoter, methyl acetate and lithium iodide to produce acetic acid and said acetic acid is recovered from the effluent of said reactor by concentrating the effluent into a variety of process streams comprising one or more of the components of said catalyst solution and product acetic acid wherein said streams contain lithium and corrosion metal contaminants, the improvement comprising: removing said metal contaminants from at least one of said process streams by intimately contacting said stream with a cation exchange resin in the lithium form and recovering a process stream of substantially reduced metal contaminant content.

11. The process of claim 10 wherein said resin is a strong-acid cation exchange resin.

12. The process of claim 10 wherein said contacting is effected by passing the catalyst solution through a fixed-bed column of said resin.

13. The process of claim 10 wherein said resin is regenerated after exhaustion by washing with a lithium salt.

14. The process of claim 13 wherein said lithium salt is lithium acetate.

15. The process of claim 13 wherein said lithium salt is dissolved in a regeneration solution of water and acetic acid.

16. The process of claim 15 wherein said acetic acid comprises from about 0.1 to 95% by weight of said regeneration solution.

17. The process of claim 16 wherein said acetic acid comprises about 1 to 20 wt. % of said regeneration solution.

18. The process of claim 15 wherein said lithium acetate is present in amounts of from about 1 to 20 wt. %.

* * * * *